United States Patent [19]

Joseph et al.

[11] 4,120,954
[45] Oct. 17, 1978

[54] 2,2',2''-[S-PHENENYLTRIS(CAR-BONYLIMINO)]TRIS-2-DEOXY-D-GLUCOPYRANOSE AND SALTS THEREOF

[75] Inventors: Joseph Peter Joseph, Cliffside Park, N.J.; Seymour Bernstein, New City, N.Y.

[73] Assignee: American Cyanamid Company, Stamford, Conn.

[21] Appl. No.: 784,202

[22] Filed: Apr. 4, 1977

[51] Int. Cl.$^2$ ............................................. A61K 31/70
[52] U.S. Cl. ........................................ 424/180; 536/4; 536/18; 536/53; 536/54; 536/115; 536/118; 536/55

[58] Field of Search ................. 536/4, 18, 53, 54, 55, 536/115; 424/180

[56] References Cited

U.S. PATENT DOCUMENTS 3,118,875  1/1964  Adams .................................. 536/18

*Primary Examiner*—Johnnie R. Brown
*Assistant Examiner*—Blondel Hazel
*Attorney, Agent, or Firm*—Claude J. Caroli

[57] ABSTRACT

2,2',2''-[s-Phenenyltris(carbonylimino)]tris-2-deoxy-D-glucopyranose and salts thereof, useful as complement inhibitors.

21 Claims, No Drawings

2,2',2''-[S-PHENENYLTRIS(CARBONYLIMINO)]TRIS-2-DEOXY-D-GLUCOPYRANOSE AND SALTS THEREOF

DESCRIPTION OF THE INVENTION

This invention is concerned with compounds of the formula:

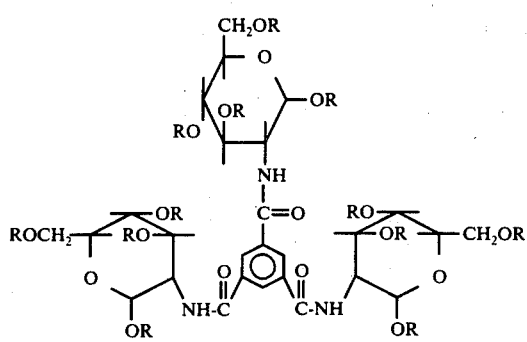

wherein R is selected from the group consisting of hydrogen, acetyl, —SO₃Na and —SO₃H.N(CH₃)₃.

A preferred embodiment of the instant invention encompasses those compounds wherein R is selected from the group consisting of hydrogen and acetyl. Another preferred embodiment encompasses those compounds wherein R is selected from the group consisting of —SO₃H.N(CH₃)₃ and —SO₃Na.

The compounds of the present invention may be prepared by reacting 2-amino-2-deoxy-D-glucopyranose tetraacetate with 1,3,5-benzene tricarboxylic acid chloride in an organic solvent such as acetonitrile and then collecting the 2,2',2''-[s-phenenyltris(carbonylimino)]tris-2-deoxy-β-D-glucopyranose dodecaacetate. This compound is then treated with ammonia saturated methanol to give the product 2,2',2''-[s-phenenyltris(carbonylimino)]tris-2-deoxy-D-glucopyranose.

This latter product is treated with trimethylamine sulfur trioxide in dimethylformamide at from about 60° to about 70° C for several hours and the product 2,2',2''-[s-phenenyltris(carbonylimino)]-tris-2-deoxy-D-glucopyranose dodecakis (H-sulfate) dodecasalt with trimethylamine is recovered by conventional procedures.

This latter compound is treated with sodium acetate and extracted with ethanol giving the product 2,2',2''-[s-phenenyltris(carbonylimino)]tris-2-deoxy-D-glucopyranose-(H-sulfate) dodecasodium salt.

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1g, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in body processes can be found in, for example, Bull. World Health Org., 39, 935-938 (1968); Ann. Rev. Medicine, 19, 1-24 (1968); The John Hopkins Med. J., 128, 57-74 (1971); Harvey Lectures, 66, 75-104 (1972); The New England Journal of Medicine, 287, 452-454; 489-495; 545-549; 592-596; 642-646 (1972); Scientific American, 229, (No. 5), 54-66 (1973); Federation Proceedings, 32, 134-137 (1973); Medical World News, Oct. 11, 1974, pp. 53-58; 64-66; J. Allergy Clin. Immunol., 53, 298-302 (1974); Cold Spring Harbor Conf. Cell Proliferation 2/Proteases Biol. Control/229-241 (1975); Annals of Internal Medicine, 84, 580-593 (1976); "Complement: Mechanisms and Functions," Prentice-Hall, Englewood Clifs, N.J. (1976).

The complement system can be considered to consist of three sub-systems: (1) a recognition unit (C1g) which enables it to combine with antibody molecules that have detected a foreign invader; (2) an activation unit (C1r, C1s, C2, C4, C3) which prepares a site on the neighboring membrane; and (3) and attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain of the complement proteins, suggestions regarding the mode of complement binding to biological membranes and the manner in which complement effects membrane damage are discussed in Annual Review in Biochemistry, 38, 389 (1969).

A variety of substances have been disclosed as inhibiting the complement system, i.e., as complement inhibitors. For example, the compounds 3,3'-ureylenebis-[6-(2-amino-8-hydroxy-6-sulfo-1-naphthylazo)]benzenesulfonic acid, tetrasodium salt (chlorazol fast pink), heparin and a sulphated dextran have been reported to have an anticomplementary effect, British Journal of Experimental Pathology, 33, 327–339 (1952). The compound 8-(3-benzamido-4-methylbenzamido)naphthalene-1,3,5-trisulfonic acid (Suramin) is described as a competitive inhibitor of the complement system, Clin. Exp. Immunol., 10, 127–138 (1972). German Pat. No. 2,254,893 or South African Pat. No. 727,923 discloses certain 1-(diphenylmethyl)-4-(3-phenylallyl)piperazines useful as complement inhibitors. Other chemical compounds having complement inhibiting activity are disclosed in, for example, Journal of Medicinal Chemistry, 12, 415–419; 902–905; 1049–1052; 1053–1056 (1969); Canadian Journal of Biochemistry, 47, 547–552 (1969); The Journal of Immunology, 93, 629–640 (1964); The Journal of Immunology, 104, 279–288 (1970); The Journal of Immunology, 106, 241–245 (1971); and The Journal of Immunology, 111, 1061–1066 (1973).

It has been reported that the known complement inhibitors epsilon-aminocaproic acid, Suramin and tranexamic acid all have been used with success in the treatment of hereditary angioneurotic edema, a disease state resulting from an inherited deficiency or lack of function of the serum inhibitor of the activated first component of complement (C1 inhibitor), The New England Journal of Medicine, 286, 808–812 (1972).

The compounds of the present invention may be administered internally, e.g., orally, intra-articularly or parenterally, e.g., intra-articular, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every 6 hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

While in general the sodium salts of the acids of the invention are suitable for parenterial use, other salts may also be prepared, such as those of primary amines, e.g., ethylamine; secondary amines, e.g., diethylamine or diethanol amine; tertiary amines, e.g., pyridine or triethylamine or 2-dimethylaminomethyl-dibenzofuran; aliphatic diamines, e.g., decamethylenediamine; and aromatic diamines, can be prepared. Some of these are soluble in water, others are soluble in saline solution, and still others are insoluble and can be used for purposes of preparing suspensions for injection. Furthermore as well as the sodium salt, those of the alkali metals, such as potassium and lithium; of ammonia; and of the alkaline earth metals, such as calcium or magnesium, may be employed. It will be apparent, therefore, that these salts embrace, in general derivatives of salt-forming cations.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate dicalcium phosphate, gums, or similar materials as nontoxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form, as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test, Code 026 (C1 inhibitor) — This test measures the ability of activated human C1 to destroy fluid phase human C2 in the presence of C4 and appropriate dilutions of the test compound. An active inhibitor protects C2 from C1 and C4; (ii) Test, Code 035 (c3–C9 inhibitor) — This test determines the ability of the late components of human complement (C3–C9) to lyse EAC 142 in the presence of appropriate dilutions of the test compound. An active inhibitor protects EAC 142 from lysis by human C3–C9; (iii) Test, Code 036 (C-Shunt inhibitor) — In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test — Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg is then reported, unless otherwise stated; (v) Forssman Shock Test — Lethal shock is produced in guinea pigs by an i.v. injection of anti-Forssman antiserum and the harmonic mean death time of treated guinea pigs is compared with that of simultaneous controls; (vi) Complement Level Reduction Test — In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test — Here, appropriate amounts of the test compound are added to a pool of guinea pig serum in vitro, after which the undiluted serum capillary tube assay referred to above is run. The concentration of compound inhibiting 50% is reported.

With reference to Table I, guinea pigs weighing about 300 g were dosed intravenously (i.v.) or intraperitoneally (i.p.) with 200 mg/kg of the test compound dissolved in saline and adjusted to pH 7-8. One hour after dosing, the guinea pigs were decapitated, blood was collected and the serum separated. The serum was tested for whole complement using the capillary tube assay. Percent inhibition was calculated by comparison with simultaneous controls. The results appear in Table I together with results of tests, code 026, 035, 036, Cap 50, % inhibition and Forssman shock. Table I shows that the compounds of the invention possess highly significant in situ and in vivo, complement inhibiting activity in warm-blooded animals.

TABLE I

| Compound | Biological Activities | | | |
| --- | --- | --- | --- | --- |
| | C1 026* Wells | C-Late 035* Wells | Shunt Inhibition 036* Wells | Cap 50* |
| 2,2′,2″-[s-Phenenyltris(carbonylimino)]-tris-2-deoxy-D-glucopyranose dodecakis (H-sulfate) dodecasalt with trimethylamine | +9, +5 | +1, +5 | +3 | 494 |
| 2,2′,2″-[s-Phenenyltris(carbonylimino)]-tris-2-deoxy-D-glucopyranose (H-sulfate) dodecasodium | +9, +5 | +1, +5 | +3 | 169 |

*Code designations for tests employed as referred to herein.

EXAMPLE 1

2,2′,2″-[s-Phenenyltris(carbonylimino)]tris-2-deoxy-D-glucopyranose

An 8.5 g portion of 2-amino-2-deoxy-D-glucopyranose tetraacetate [Bergman and Zewar, Ber., 64, 975 (1931)] is dissolved in 100 ml of acetonitrile. A 2.2 g portion of pyridine is added. A 1.96 g portion of 1,3,5-benzene tricarboxylic acid chloride is added. The mixture is stirred overnight, filtered, the filtrate is washed with acetonitrile and then poured into 600 ml of ice water. The solid is collected, dissolved in chloroform and filtered. The filtrate is evaporated and hexane is added. The solid is collected giving 5.5 g of 2,2′,2″-[s-phenenyltris(carbonylimino)]tris-2-deoxy-β-D-glucopyranose dodecaacetate.

A 4.0 g portion of the above compound is dissolved in 40 ml of methanol saturated with ammonia and the mixture is allowed to stand 4 hours. The solid is collected, washed with methanol, absolute ethanol and ether and dried giving the final desired product.

EXAMPLE 2

2,2′,2″-[s-Phenenyltris(carbonylimino)]tris-2-deoxy-D-glucopyranose dodecakis (H-sulfate) dodecasalt with trimethylamine A 1.0 g portion of 2,2′,2″-[s-phenenyltris)carbonylimino)]tris-2-deoxy-D-glucopyranose is dissolved in 15 ml of dimethylformamide. A 2.9 g portion of trimethylamine sulfur trioxide is added and the mixture is stirred for 18 hours at 60°–70° C. The supernatant liquid is decanted and triturated with fresh dimethylformamide and then absolute ethanol. The solid is collected, washed with absolute ethanol, then ether, and dried giving the desired product as a tan amorphous solid, $[\alpha]_D^{25} + 67° \pm 1$ (H$_2$O).

EXAMPLE 3

2,2′,2″-[s-Phenenyltris(carbonylimino)]tris-2-deoxy-D-glucopyranose dodecakis (H-sulfate) dodecasodium salt A 750 mg portion of 2,2′,2″-[s-phenenyltris(carbonylimino)]tris-2-deoxy-D-glucopyranose, dodecakis (H-sulfate) dodecasalt with trimethylamine is dissolved in 5 ml of water. A 2.5 ml portion of 30% sodium acetate in water is added. The mixture is treated with carbon, filtered through diatomaceous earth and the filtrate is poured into 250 ml of ethanol. The supernatant liquid is discarded and the remainder is filtered. The solid is dissolved in 2 ml of water and 12 ml of 30% sodium acetate solution is added. Ethanol is added until the solution is turbid. The dark oil is discarded. The supernatant is poured with stirring into 200 ml of ethanol. The solid is collected giving the desired product as a tan amorphous solid, $[\alpha]_D^{25} + 69° \pm 1$ ($H_2O$).

EXAMPLE 4

| Preparation of Compressed Tablet | |
|---|---|
| Ingredient | mg/Tablet |
| Active Compound | 0.5–500 |
| Dibasic Calcium Phosphate N.F. | qs |
| Starch USP | 40 |
| Modified Starch | 10 |
| Magnesium Stearate USP | 1–5 |

EXAMPLE 5

| Preparation of Compressed Tablet - Sustained Action | |
|---|---|
| Ingredient | mg/Tablet |
| Active Compound as Aluminum Lake*, Micronized | 0.5–500 (as acid equivalent) |
| Dibasic Calcium Phosphate N.F. | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5-30%.

EXAMPLE 6

| Preparation of Hard Shell Capsule | |
|---|---|
| Ingredient | mg/Capsule |
| Active Compound | 0.5–500 |
| Lactose, Spray Dried | qs |
| Magnesium Stearate | 1–10 |

EXAMPLE 7

| Preparation of Oral Liquid (Syrup) | |
|---|---|
| Ingredient | % W/V |
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 8

| Preparation of Oral Liquid (Elixir) | |
|---|---|
| Ingredient | % W/V |
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 9

| Preparation of Oral Suspension (Syrup) | |
|---|---|
| Ingredient | % W/V |
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |

-continued

| Preparation of Oral Suspension (Syrup) | |
|---|---|
| Ingredient | % W/V |
| Propyl Paraben USP | 0.02 |
| Liquid Sugar | 75.0 |
| Purified Water qs ad | 100.0 |

EXAMPLE 10

| Preparation of Injectable Solution | |
|---|---|
| Ingredient | % W/V |
| Active Compound | 0.05–5 |
| Benzyl Alcohol N.F. | 0.9 |
| Water for Injection | 100.0 |

EXAMPLE 11

| Preparation of Injectable Oil | |
|---|---|
| Ingredient | % W/V |
| Active Compound | 0.05–5 |
| Benzyl Alcohol | 1.5 |
| Sesame Oil qs ad | 100.0 |

EXAMPLE 12

| Preparation of Intra-Articular Product | |
|---|---|
| Ingredient | Amount |
| Active Compound | 2–20 mg |
| NaCl (physiological saline) | 0.9% |
| Benzyl Alcohol | 0.9% |
| Sodium Carboxymethylcellulose | 1–5% |
| pH adjusted to 5.0–7.5 | |
| Water for Injection qs ad | 100% |

EXAMPLE 13

| Preparation of Injectable Depo Suspension | |
|---|---|
| Ingredient | % W/V |
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6–8 | qs |
| Water for Injection qs ad | 100.0 |

We claim:

1. A compound of the formula:

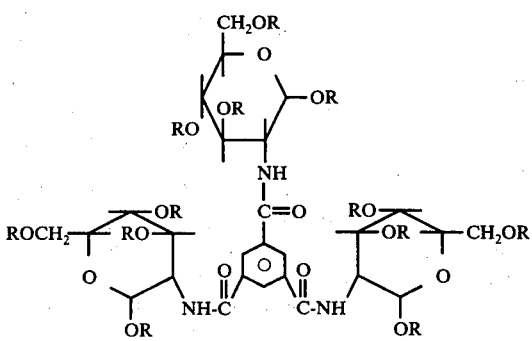

wherein R is selected from the group consisting of hydrogen, acetyl, —SO₃Na, —SO₃H.N(CH₂CH₃)₃ and —SO₃H.N(CH₃)₃.

2. A compound according to claim 1, wherein R is selected from the group consisting of hydrogen and acetyl.

3. A compound according to claim 1, wherein R is selected from the group consisting of —SO₃Na and —SO₃H.N(CH₃)₃.

4. The compound according to claim 2, 2,2',2''-[s-phenenyltris(carbonylimino)]tris-2-deoxy-D-glucopyanose.

5. The compound according to claim 2, 2,2',2''-[s-phenenyltris(carbonylimino)]tris-2-deoxy-D-glucopyranose dodecaacetate.

6. The compound according to claim 3, 2,2',2''-[s-phenenyltris(carbonylimino)]tris-2-deoxy-D-glucopyranose dodecakis (H-sulfate) dodecasodium salt.

7. The compound according to claim 3, 2,2',2''-[s-phenenyltris(carbonylimino)]tris-2-deoxy-D-glucopyranose dodecakis (H-sulfate) dodecasalt with trimethylamine.

8. A method of inhibiting the complement system in body fluid which compresses subjecting said body fluid to the action of an effective complement inhibiting amount of a compound of the formula:

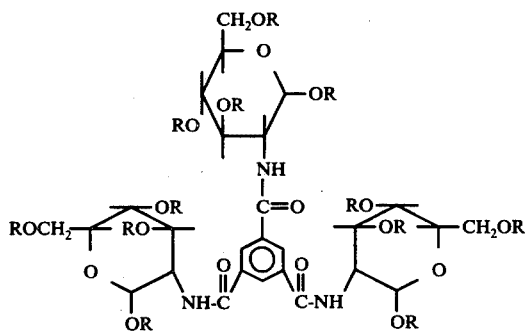

wherein R is selected from the group consisting of hydrogen, acetyl, —SO₃Na, —SO₃H.N(CH₂CH₃)₃ and —SO₃H.N(CH₃)₃.

9. The method according to claim 8, wherein said compound is 2,2',2''-[s-phenenyltris(carbonylimino)]-tris-2-deoxy-D-glucopyranose.

10. The method according to claim 8, wherein said compound is 2,2',2''-[s-phenenyltris(carbonylimino)]-tris-2-deoxy-D-glucopyranose dodecaacetate.

11. The method according to claim 8, wherein said compound is 2,2',2''-[s-phenenyltris(carbonylimino)]-tris-2-deoxy-D-glucopyranose dodecakis (H-sulfate) dodecasodium salt.

12. The method according to claim 8, wherein said compound is 2,2',2''-[s-phenenyltris(carbonylimino)]-tris-2-deoxy-D-glucopyranose dodecakis (H-sulfate) dodedcasalt with trimethylamine.

13. The method according to claim 8, wherein said body fluid is blood serum.

14. A method of inhibiting the complement system in a warm-blooded animal which compresses internally administering to said animal an effective complement inhibiting amount of a compound of the formula:

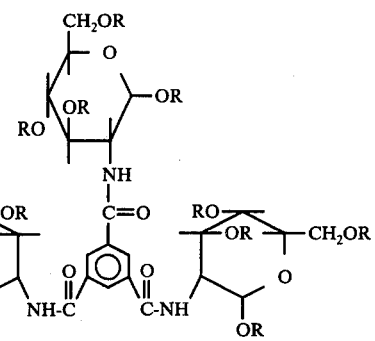

wherein R is selected from the group consisting of hydrogen, acetyl, —SO₃Na, —SO₃H.N(CH₂CH₃)₃ and —SO₃H.N(CH₃)₃.

15. The method according to claim 14, wherein said compound is 2,2',2''-[s-phenenyltris(carbonylimino)]-tris-2-deoxy-D-glucopyranose.

16. The method according to claim 14, wherein said compound is 2,2',2''-[s-phenenyltris(carbonylimino)]-tris-2-deoxy-D-glucopyranose dodecaacetate.

17. The method according to claim 14, wherein said compound is 2,2',2''-[s-phenenyltris(carbonylimino)]-tris-2-deoxy-D-glucopyranose dodecakis (H-sulfate) dodecasodium salt.

18. The method according to claim 14, wherein said compound is 2,2',2''-[s-phenenyltris(carbonylimino)]-tris-2-deoxy-D-glucopyranose dodecakis (H-sulfate) dodecasalt with trimethylamine.

19. The method according to claim 14, wherein said compound is administered intra-articularly.

20. A method for preparing a compound of the formula:

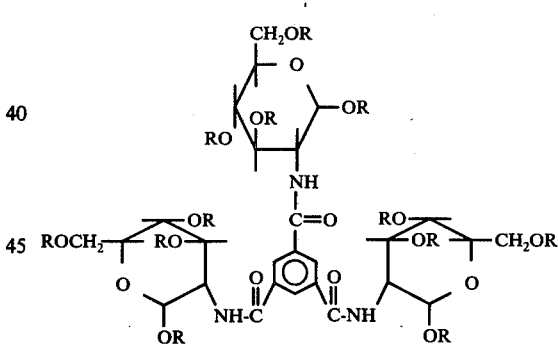

wherein R is selected from the group consisting of hydrogen, acetyl, —SO₃Na, —SO₃H.N(CH₂CH₃)₃ and —SO₃H.N(CH₃)₃; which comprises reacting 2-amino-2-deoxy-D-glucopyranose tetracetate with 1,3,5-benzenetricarboxylic acid chloride in a suitable organic solvent and collecting the 2,2',2''-[s-phenenyltris(carbonylimino)]tris-2-deoxy-D-glucopyranose; treating said D-glucose with trimethylamine sulfur trioxide in dimethylformamide at from about 60° to about 70° C for several hours and recovering the 2,2',2''-[s-phenenyltris(carbonylimino)]-2-deoxy-D-glucopyranose dodecakis (H-sulfate) dodecasalt with trimethylamine; and treating said dodecasalt with sodium acetate and extracting with ethanol to obtain 2,2',2''-[s-phenenyltris(carbonylimino)]tris-2-deoxy-D-glucopyranose dodecakis (H-sulfate) dodecasodium salt.

21. The method according to claim 20, wherein said suitable organic solvent is acetonitrile.

* * * * *